United States Patent [19]

Silver et al.

[11] Patent Number: 5,196,185

[45] Date of Patent: Mar. 23, 1993

[54] COLLAGEN-BASED WOUND DRESSING AND METHOD FOR APPLYING SAME

[75] Inventors: Fred Silver, Bangor, Pa.; Vinay Sharma, Long Valley, N.J.; Dieter R. Berndt, Allenwood, N.J.; Louis E. Marn, Morris Plains, N.J.

[73] Assignee: Micro-Collagen Pharmaceutics, Ltd., Long Valley, N.J.

[21] Appl. No.: 405,520

[22] Filed: Sep. 11, 1989

[51] Int. Cl.$^5$ ............................................. A61L 9/04
[52] U.S. Cl. ...................................... 424/45; 514/801; 424/428
[58] Field of Search .................. 241/184; 424/45, 499; 128/156; 604/368; 514/778, 734; 530/356

[56] References Cited

U.S. PATENT DOCUMENTS

| | | | |
|---|---|---|---|
| 3,008,657 | 9/1957 | Szegvari | 241/184 |
| 3,577,516 | 12/1969 | Gould | 424/45 |
| 3,628,974 | 12/1971 | Battista | 530/356 |
| 3,800,792 | 4/1974 | McKnight | 128/156 |
| 3,932,602 | 1/1976 | Sweger | 424/45 |
| 4,453,939 | 6/1984 | Zimmerman | 604/368 |
| 4,495,168 | 1/1985 | Schmolka | 424/45 |
| 4,524,064 | 6/1985 | Nambu | 514/778 |
| 4,863,856 | 9/1989 | Dean | 530/356 |
| 4,895,724 | 1/1990 | Cardinal | 424/499 |
| 4,895,727 | 1/1990 | Allen | 514/734 |
| 4,929,442 | 5/1990 | Powell | 424/85.4 |
| 4,952,404 | 8/1990 | Vallee | 424/499 |

*Primary Examiner*—Thurman K. Page
*Assistant Examiner*—William E. Benston, Jr.
*Attorney, Agent, or Firm*—Louis E. Marn

[57] ABSTRACT

There is disclosed a collagen preparation formed from a collagen selected from the group consisting of Type I collagen, Type III collagen and mixtures thereof into a particulate collagen of a particle size of from about 1 to 50 μm, preferably 5 to 25 μm into a delivery system, such as an aerosol, and thus in sprayable form as a wound dressing alone, or with releasing drugs or other active agents. The particulate collagen comprises up to about 20% by weight of the resulting delivery system.

12 Claims, No Drawings

COLLAGEN-BASED WOUND DRESSING AND METHOD FOR APPLYING SAME

BACKGROUND OF THE INVENTION (1) Abstract of the Disclosure

This invention relates to drug delivery systems, and more particularly to collagen-based drug delivery system and process for producing same.

(2) Background of the Invention

Collagen is the major protein in animals. It has an extended history of use in the medical field primarily due to its ability to polymerize in vitro into strong fibers that can be fabricated into a number of forms. Collagen has been utilized for a variety of clinical purposes including wound treatment, hemostasis, and soft tissue augmentation. The other medical applications of collagen have been described in a recent book entitled "Biocompatibility; Interactions of Biological and Implantable Material", Volume 1, Polymers by F. H. Silver and C. J. Doillon, YCH Publishers, New York, New York, 1989.

Soluble collagen has been used as a subcutaneous implant for repairing dermatological defects such as acne scars, glabellar furrows, excision scars and other soft tissue defects. Klein, A. W. J. Acad. Derm 9:224-228 (1983); Knapp, T. R., Luck, E. and Daniels, J. R. J. Surg. Res 23:96-105 (1977); and Kaplan, E. N., Falces, E. and Toileth, H. Clinical Utilization of Injectable Collagen, Ann. Plast. Surg., 10:437-151 (1983). Although it appears that this implant is readily accepted, the repair of the defects is temporary and patients need additional treatment after 6 to 18 months. There were also a number of adverse tissue responses after utilization of soluble collagen. Castrow, F. F. and Kruil, E. A. Injectable Collagen Implant—Update, J. Am. Acad. Dermatol. 9:889-893 (1983). Labow, T. A., and Silvers, D. N Late Reactions at Zydern Skin Test Sites, Cutis 35:154-158 (1984) and Cohen, I. K. Peacock, E. E. and Chvapil, M. Editorial on Zyderm. Plas. Reconstr. Surg., 73:1 (1984).

Collagen has also been used in many forms as a wound dressing. The various forms of collagen wound dressings include collagen sponges, such as described in Artandi U.S. Pat. No. 3,157,524 and Berg et al U.S. Pat. No. 4, 320,201; and collagen/polymer film composites, such as described in McKnight et al, U.S. Pat. No. 3,800,792. However, many of these dressings are not satisfactory for the various types of full thickness wounds. Collagen films and sponges do not readily conform to varied wound shapes Further, some collagen wound dressings have poor fluid absorption properties and enhance the pooling of wound fluids.

The use of wound dressings comprised of Type I collagen have limited commercial success because of the difficulty of the physical form of the dressing. Sponge dressings are difficult to apply to deep wounds because they do not adhere well to curved surfaces. Collagen in particulate form adheres well to wounds because of its high surface areas but is difficult to apply as dry powder because of its high surface charge. In the form of thin films, fluid absorption properties of collagen lead to pooling of fluids.

OBJECTS OF THE PRESENT INVENTION

An object of the present invention is to provide particulate collagen capable of aerosol application.

Another object of the present invention is to provide collagen of high surface area.

Yet another object of the present invention is to provide enhanced particulate collagen for wound healing.

Still another object of the present invention is to apply to a wound a physiologically-acceptable amount of particulate collagen in an inert base.

A still further object of the present invention is to apply to a wound a physiologically-acceptable amount of particulate collagen in an inert base and further including an adjuvant.

A further object of the present invention is to form particulate collagen capable of aerosol dispensing.

SUMMARY OF THE INVENTION

These and other objects of the present invention are achieved by forming collagen selected from the group consisting of Type I collagen, Type III collagen and mixtures thereof into a particulate collagen of a particle size of from about 1 to 50 $\mu$m, preferably 5 to 25 $\mu$m into a delivery system, such as an aerosol, and thus in sprayable form as a wound dressing alone, or with releasing drugs or other active agents. The particulate collagen comprises up to about 20% by weight of the resulting delivery system.

DETAILED DESCRIPTION OF THE INVENTION

Collagen employed for preparation into an aerosol form for wound treatment, as well as other forms for drug delivery of the present invention are derived from native Type I or Type III collagen free of foreign materials and completely resorbable by the user's body. Such collagen is in the form of a soluble material having a molecular weight in excess of 285,000. For the purposes of the present invention, the collagen powder is in the form of discrete particles having sizes of from about 1 to 50 $\mu$m, preferably about 5 to 15 microns. The particular collagen is comprised of a network of fine fibers having thicknesses varying from about 5 to 35 microns, preferably about 10 microns. The particulate collagen absorbs 10 to 50 times its weight of water and expand 3 to 5 times in volume.

The particulate collagen is suitably prepared by milling an appropriate collagen Type I or Type III or mixtures thereof using a knife mill until the intermediate collagen particles pass through a 60 mesh screen, and then by ball-milling in an inert media, such as alcohol, into a particulate collagen for about 48 hours. The particulate collagen is mixed with a low molecular weight alcohol, such as isopropyl or denatured alcohol, at a collagen to liquid ratio of 1:5 to 1:50, preferably 1:10 to 1:15 to form a collagen dispersion of up to 20%. The collagen dispersion may be admixed with other adjuvants at this point (e.g., Type II or IV collagen, hyaluronic acid, fibronectin, other growth factors or the like). The collagen dispersion is degassed under low pressure (0.5 to 0.01 Torr) until gas bubbles no longer appear and the pH adjusted to between pH2 to 9 to maximize adsorption of the adjuvant. The resulting collagen-adjuvant-alcohol dispersion is sealed into an aerosol can pressurized with a suitable aerosol and sealed in the can under pressure.

Once the particulate collagen is formed, additional crosslinking can be effected. In accordance with the present invention, it is essential that the particulate collagen incorporated in the medicinal formulations hereof be high purity native materials, free of potentially toxic additives which may impair tissue ingrowth or preclude complete resorption upon topical application, implantation into patients. Consistent therewith, crosslinking of the particulate collagen can be effected by dispersing the collagen particles in a solution of a carbodimide (such as cyanamide or 1-ethyl-3-(3-dimethylaminopropyl)-carbodimide hydrochloride), or bifunctional N-hydroxy succinimide-derived ester (such bis(sulfosuccinimidyl) suberate), or an aqueous aldehyde, solution. The chemical crosslinking may be used in combination with severe dehydration at temperatures between 50° C. and 200° C. in a vacuum of less than 50 Torr for 2 to 92 hours. Such techniques have been described in detail in the aforesaid parent U.S. patent applications Ser. Nos. 593.733 abandoned; 843,828; pending and 875,827 pending.

The particulate collagen is incorporated in wound dressings or implants in a pharmceutically acceptable, inert carrier. The carrier may be a non-toxic base for forming an aerosol, ointment, gel, gel cream or cream incorporating the particulate collagen, such as, for example, petrolatum, propylene glycol, isopropyl myristate, or lanolin (for ointments); petrolatum or gelatin (for gels); or mono- and di-glycerides, ester waxes or stearyl alcohol (for creams).

Macromolecular materials, such as macromolecular materials selected from the group consisting of hyaluronic acid, fibronectin, collagen Types IV and V, laminin, protoglycans and mixtures thereof which affect cell growth may be incorporated into the particulate collagen dispersion. Thus, the above mentioned macromolecular materials may be added to a collagen dispersion, prior to formation of the particulate collagen, in amounts to provide of from about 0.01 to 10.0% by volume of the resulting dispersion.

Pharmacologically active agents, such as agents selected from the group consisting of platelet-derived growth factor, epidermal growth factor, transforming growth factor beta, angeogenesis factor, antibiotics, antifungal agents, spermicidal agents, hormones, enzymes, enzyme inhibitors and mixtures thereof may be incorporated in the collagen matrix for subsequent delivered to the tissue. The above mentioned agents are added to the collagen dispersion, prior to formation of the particulate collagen, in amounts varying, for example, from about 1.0 mg/ml to 0.1 mg/ml for the growth factors, and 0.0 mg/ml to 10 mg/ml for hormones, enzymes and enzyme inhibitors. The chemical crosslinking of the collagen matrix may be altered in order to alter the delivery dose of any of such agents from the collagen delivery system so that 90% of the agent is delivered in from 1 to 72 hours.

Wound dressings comprising such compositions are completely resorbed by the patient's body within about 2 to 30 days, preferably within 10 days.

Preferably, and as hereinabove noted, the wound dressings and formulations of the present invention additionally may contain macromolecular materials for promoting tissue ingrowth such as a hyaluronic acid or fibronectin (see "Fibroblast Growth on a Porous Collagen Sponge containing Hyaluronic Acid or Fibronectin", Doillon, C. J.; Silver, F. H. and Berg, R. A., Biomaterials 8:195–200), or mixtures thereof. It is believed that these materials, or other tissue growth-simulating factors, e.g. transforming growth factor beta (see Raghaw, R., Postelthwaite, A. E., Keski-Oja, J., Moses, H. L., and Kang, A. H. (1987) 79:1285–1288) or platelet-derived growth factor (Sato, G. H. Ross, R. eds. Hormones and Cell Culture. Books A and B. New York, Cold Springs Harbor), in admixture with the collagen powder, promotes fibroblast synthesis of extracellular matrix material (TGFB) or stimulate cell division (PDGF).

EXAMPLES OF THE INVENTION

The specific nature of the compositions of the present invention will be more fully apparent from consideration of the following specific examples of preferred embodiments thereof. In the examples, as in the preceding description, all parts and percentages are given by weight unless otherwise indicated.

EXAMPLE I 10.0 g. sample of purified Collagen Type I is added to a ball-mill with the subsequent addition of 90.0 g of denatured alcohol (SDA 40-2). Milling is effected for 48 hours to prepare a smooth dispersion of collagen powder of a particle size of from 0.1 to 50 μm.

EXAMPLE II 5.0 g. of the collagen powder of EXAMPLE I is introduced into a 2 ounce tared aerosol can and a valve assembly crimped into the can. The valve assembly is comprised of 2 X 20/1000 stem with a 20/1000 stainless steel spring. The valve body is 62/1000 in dimensions with a 30/1000 with a vapor tap conical cup, epon-coated. The internal diameter of the dip tube is 50/1000. 35 g. of Propellant A46 ®* is added to the tared aerosol can. A 25/1000 Standard taper (ST) actuator (Precision Valve Company) is inserted into the valve assembly. The actuator is pushed to generate a white spray of a collagen-based material.

* a registered trademark of Fluid Packaging Inc. (comprising isobutane, propane and n-butane).

EXAMPLE III 2.0 g. sample of purified Collagen I is added to a ball-mill together with 98.0 g of isopropyl Alcohol. Milling is effected for 48 hours to prepare a suspendable dispersion.

EXAMPLE IV 5.0 g. of particulate collagen of EXAMPLE III is introduced into a tared 2 ounce aerosol can and a valve crimped therein. 35.0 g. of Propellent A46 ® is added to the tared aerosol can which is further processed in EXAMPLE II. Actuation results in a spray leaving a transluscent film on human skin.

EXAMPLE V

An Anti-Itch Spray is prepared of the following ingredients:

| Diphenhydramine HCl | 2.0 g. |
| Collagen Type I | 10.0 g. |
| Propylene Glycol USP | 3.0 g. |
| Alcohol SDA 40-2 | 85.0 g. |
| | 100.0 g. |

EXAMPLE VI

An athlete foot spray is prepared of the following ingredients:

| | |
|---|---|
| Miconazole nitrate | 2.0 g. |
| Collagen Type I | 10.0 g. |
| Alcohol SDA 40-2 | 88.0 g. |
| | 100.0 g. |

The ingredients are ball-milled for 48 hours. 5.0 g. of the resulting material is introduced into a tared 2 ounce aerosol can and valve crimped therein. 35.00 g. of Propellant A46® is added to the tared aerosol can which is processed as described in EXAMPLE II. Actuation provides a white spray leaving a translucent film on human skin.

EXAMPLE VII

An Acne Treatment Gel is prepared of the following ingredients:

| | |
|---|---|
| Hydrous Benzoyl peroxide | 10.0 g. |
| Collagen Type I Dispersion (10% w/w) | 50.0 g. |
| Hydroxyl propyl methylcellulose USP | 3.0 g. |
| Purified water | 37.0 |
| | 100.0 g. |

Hydroxyl propyl methylcellulose is dispersed in hot water (70° C.). When temperature is reduced to 40° C., hydrous benzyl peroxide and collagen Type I dispersion are added with stirring.

EXAMPLE VIII

An Analgesic/Anti-inflamatory Spray Bandage is prepared of the following ingredients:

| | |
|---|---|
| Acetylsalicylic acid USP | 10.0 g. |
| Polyvinylpyrollidone USP | 5.0 g. |
| Collagen Type I | 10.0 g. |
| Propylene Glycol USP | 3.0 g. |
| Alcohol SDA-40-2 | 72.0 g. |
| | 100.0 g. |

The ingredients are ball-milled for 48 hours. 5.0 g. of the resulting material is introduced into a tared 2 ounce aerosol can and valve crimped therein. 35.0 g. of Propellant A46® is added to the tared aerosol can which is processed as described in EXAMPLE II. Actuation provides a white spray leaving a transluscent film on human skin.

In accordance with the present invention, the collagen microparticles are sufficiently small to be airlessly sprayed through an orifice of at least 50, generally 500 $\mu$m to form a dry film on a surface of skin or wounds. Such film is sufficient to permit oxygen diffusion for promoting wound healing and tissue growth, as well as to provide wound repair by stimulating accumulation of inflammatory and connective tissue cells in the wound, absorption of fluid from the wound, and by limiting bacterial penetration from the air.

A further advantage of the wound dressing and composition for soft tissue augmentation of the present invention is its ability to conform to varied sizes and shapes of wounds. Many wounds, due to their odd sizes and shapes, are not conducive to sponge or film dressings.

The rate of wound healing is further enhanced by the addition to the particulate collagen macromolecules capable of promoting tissue ingrowth, such as hyaluronic acid or fibronectin. Doillon et al. (1987) Biomaterials 8:195-200; and Doillon and Silver (1986) Biomaterials 7:3-8. Hyaluronic acid in the collagen matrix encourages cellular infiltration into the the pores and channels of the matrix. Fibronectin induces ce attachment to the collagen fibers of the matrix. Thus, incorporation of hyaluronic acid and/or fibronectin into the particulate collagen composition enhances cell mobility and replication in the collagen matrix, and promotes cell ingrowth into the wounds or deffective tissues treated therewith. Other macromolecules, such as collagen types IV and Y, laminin, and proteoglycans can also be added to the particles to alter cell growth.

Another advantage of the present invention is the incorporation into and the subsequent delivery from the particulate collagen of pharmacological agents such as platelet-derived growth factor, epidermal growth factor, transforming growth factor beta, angeogenesis factor, anti-hystammines, analgesics, anti-inflammatory agents, antibiotics, antifungal agents, spermicidal agents, hormones, enzymes, or enzyme inhibitors.

While the invention has been described in connection with an exemplary embodiment thereof, it will be understood that many modifications will be apparent to those of ordinary skill in the art; and that this application is intended to cover any adaptations of variations thereof. Therefore, it is manifestly intended that this invention be only limited by the claims and the equivalents thereof.

What is claimed is:

1. A method of wound treatment, which comprises: applying to such a wound particulate collagen in a carrier, said particulate collagen being of a particle size of from about 1 to 50 $\mu$m.

2. The method of wound treatment as defined in claim 1 wherein said carrier is selected from the group consisting of an ointment, gel, gel cream, cream, aerosol and occlusive film.

3. The method of wound treatment as defined in claim 1 wherein said carrier is an aerosol.

4. The method of wound treatment as defined in claim 1 or 2 and further including a macromolecular material selected from the group consisting of hyaluronic acid, fibronectin, particulate collagen Type IV, particulate collagen Type V, laminin, protoglycans and mixtures thereof.

5. The method of wound treatment as defined in claim 1 or 2 and further including a pharmacologically active agent selected from the group consisting of platelet-derived growth factors, epidermal growth factors, transforming growth factor beta, angeogenesis factor, antibiotics, antifungal agents, spermicidal agents, hormone enzymes, enzyme inhibitors, antihistamines, analgesics and anti-inflammatory agents.

6. A wound dressing, which comprises: collagen in a carrier, said particulate collagen being of a particle size of from about 1 to 50 $\mu$m.

7. The wound dressing as defined in claim 6 and further including a macromolecular material in an amount of from 0.01 to 10.0% by volume thereof.

8. The wound dressing as defined in claim 7 wherein said macromolecular material is selected from the group consisting of hyaluronic acid, fibronectin, particulate collagen Type IV, particulate collagen Type V, laminin, protoglycans and mixtures thereof.

9. The wound dressing as defined in claim 6 and further including a pharmacologically active agent.

10. The wound dressing as defined in claim 9 wherein said pharmacologically active agent is selected from the group consisting of platelet-derived growth factors, epidermal growth factors, transforming growth factor beta, angeogenesis factor, antibiotics, antifungal agents, spermicidal agents, hormones, enzymes and enzyme inhibitors.

11. The wound dressing as defined in claim 7 or 8 and further including a pharmacologically active agent.

12. The wound dressing as defined in claim 11 wherein said pharmacologically active agent is selected from the group consisting of platelet-derived growth factors, epidermal factors, transforming growth factor beta, aneogenesis factor, antibiotics, antifungal agents, spermicidal agents, hormones, enzymes and enzyme inhibitors.

* * * * *